(12) United States Patent
Monty et al.

(10) Patent No.: US 9,603,560 B2
(45) Date of Patent: Mar. 28, 2017

(54) FLEXIBLE ELECTRODE FOR DETECTING CHANGES IN TEMPERATURE, HUMIDITY, AND SODIUM ION CONCENTRATION IN SWEAT

(71) Applicant: The University of Akron, Akron, OH (US)

(72) Inventors: Chelsea N Monty, Copley, OH (US); Evan K Wujcik, Warren, RI (US); Nathaniel Jacob Blasdel, Akron, OH (US)

(73) Assignee: The University of Akron, Akron, OH (US)

( * ) Notice: Subject to any disclaimer, the term of this patent is extended or adjusted under 35 U.S.C. 154(b) by 435 days.

(21) Appl. No.: 13/751,199

(22) Filed: Jan. 28, 2013

(65) Prior Publication Data

US 2013/0197319 A1    Aug. 1, 2013

Related U.S. Application Data

(60) Provisional application No. 61/590,839, filed on Jan. 26, 2012.

(51) Int. Cl.
*A61B 5/1477*    (2006.01)
*A61B 5/145*     (2006.01)
(Continued)

(52) U.S. Cl.
CPC .............. *A61B 5/1477* (2013.01); *A61B 5/01* (2013.01); *A61B 5/14517* (2013.01);
(Continued)

(58) Field of Classification Search
CPC .............. A61B 5/1477; A61B 5/14517; A61B 5/14546; A61B 5/01; A61B 5/443; A61B 5/6804
See application file for complete search history.

(56) References Cited

U.S. PATENT DOCUMENTS

2007/0213611 A1*  9/2007  Simpson et al. .............. 600/365
2007/0270675 A1* 11/2007  Kane et al. ................... 600/315
(Continued)

FOREIGN PATENT DOCUMENTS

EP    0650708 B1    6/2000

OTHER PUBLICATIONS

LeGrys, Vicky A. et al, "Diagnostic Sweat Testing: The Cystic Fibrosis Foundation Guidelines", Journal of Pediatrics, vol. 151, No. 1, pp. 85-89, Jul. 2007.
(Continued)

*Primary Examiner* — Christine H Matthews
(74) *Attorney, Agent, or Firm* — Renner Kenner Greive Bobak Taylor & Weber

(57) ABSTRACT

The present invention includes a flexible sensor suitable for contact with skin comprising: a nanocomposite; and a top layer; where the sensor provides in-situ detection in sweat or other aqueous body fluids at the skin surface of at least one physiological parameter selected from the group consisting of a physiological salt component, temperature, moisture, humidity, or combinations thereof. The present invention further includes a method of fabricating a flexible sensor suitable for contact with skin comprising: electrospinning at least one polyamide-producing monomer to form a non-conductive polyamide substrate; attaching at least one plurality of conductive nanoscale attachments, wherein the nanoscale attachments are selected from nanotubes, nanoparticles, or combinations thereof, to form an intermediate layer; and functionalizing the intermediate layer to form a top layer.

15 Claims, 13 Drawing Sheets

(51) Int. Cl.
*A61B 5/01* (2006.01)
*A61B 5/00* (2006.01)
*A61B 10/00* (2006.01)
*B82Y 5/00* (2011.01)
*B82Y 15/00* (2011.01)

(52) U.S. Cl.
CPC .......... *A61B 5/14546* (2013.01); *A61B 5/443* (2013.01); *A61B 5/6804* (2013.01); *A61B 10/0064* (2013.01); *A61B 2562/0209* (2013.01); *A61B 2562/029* (2013.01); *A61B 2562/0285* (2013.01); *A61B 2562/125* (2013.01); *B82Y 5/00* (2013.01); *B82Y 15/00* (2013.01); *Y10S 977/92* (2013.01)

(56) References Cited

U.S. PATENT DOCUMENTS

2007/0276208 A1* 11/2007 Connelly et al. ............. 600/309
2010/0030045 A1*  2/2010 Gottlieb et al. ............. 600/347

OTHER PUBLICATIONS

Wujcik, Evan, Nathaniel Blasdel, Daniel Trowbridge, and Chelsea Monty. "Ion Sensor for the Quantification of Sodium in Sweat Samples." IEEE Sensors Journal (2013): 1-1. doi:10.1109/JSEN.2013.2257168; published Apr. 5, 2013.

* cited by examiner

FLEXIBLE ELECTRODE FOR DETECTING CHANGES IN TEMPERATURE, HUMIDITY, AND SODIUM ION CONCENTRATION IN SWEAT

CROSS-REFERENCE TO RELATED APPLICATION

This application claims the benefit of U.S. Provisional Application No. 61/590,839 filed Jan. 26, 2012.

FIELD OF THE INVENTION

The present invention is directed to a flexible or wearable sensor for real-time screening and/or diagnosis of medical conditions. The sensor of the present invention is useful in measurement and/or monitoring of ion concentration, humidity, and temperature at the surface of the skin. Such amperometric sensors have wide applicability in medical devices as biosensors.

BACKGROUND OF THE INVENTION

The development of a flexible sensing platform for biomedical device and diagnostic applications is critical to advancing current diagnostic and analytical techniques used in the healthcare field. Electronic fabrics or smart textiles are at a forefront of biomedical research for a variety of ambulatory, diagnostic, and therapeutic devices. Two examples where such a sensing platform would be beneficial are in cystic fibrosis diagnosis and monitoring stump-socket conditions for amputee patients. The sensing platform of the present invention could also be extended to other biomedical applications such as wound healing.

Cystic fibrosis (CF) is a life-threatening genetic disease that attacks the lungs, pancreas, liver, and intestines and affects the lives of over 26,000 Americans, including nearly 900 newly diagnosed cases in 2010. CF is prevalent among Caucasians, but has been found to affect all racial and ethnic groups. The Cystic Fibrosis Foundation estimates that one in 3,500 newborns have the disease, which is not diagnosed until a median age of 5 months old. The disease causes a thick, sticky mucus to build up in some organs and organ systems, causing complications and even possibly organ failure or death. This disorder does not discriminate, as it can be passed to both males and females with approximately a 50:50 distribution. The gene presents with over 1,200 different mutations, many of which are specific to individual family lines. This makes identifying and diagnosing both affected individuals, as well as carriers of the disease, extremely important in tracing the dysfunctional genotypes. CF patients have an abnormally high transport of sodium and chloride ions across the epithelium and therefore the disease is most commonly diagnosed by sweat electrolyte testing, which the Cystic Fibrosis Foundation recommends as the standard of CF diagnosis in children.

Suspected descriptions of CF have been documented since the late 1500's. However, the disease was not specifically identified until the late 1930's, and the sweat electrolyte diagnostic test was implemented as late as the 1950's. The identification of the CF gene did not occur until 1989, but research into its malfunction has dramatically increased since that time. This brings us to the current state of CF treatment and research, that has evolved considerably with the exception of diagnostic testing (the sweat test), which has not changed significantly for over sixty years.

The Cystic Fibrosis Foundation, as well as other medical sources, emphasizes that early diagnosis is critical in the success of treating the disease and prolonging the life expectancy of patients, making a quick and accurate diagnosis of the utmost importance. In the US, only about 70% of all cystic fibrosis patients are diagnosed before their first birthday, and only about 90% are diagnosed before their eighth birthday. These statistics are surprisingly lower throughout the world, where some affected individuals go their entire life undiagnosed.

The sweat test, which may also be referred to as the iontophoretic sweat test or sweat electrolyte test, is the current diagnostic protocol for cystic fibrosis and is described by LeGrys et al. in *The Journal of Pediatrics*, vol. 151, no. 1, pp. 85-89, July, 2007. This test is performed by applying a colorless odorless chemical (pilocarpine), that induces sweating, to the arm, leg, or foot, and stimulating the area via electrode. The sweat is then collected with a gauze or filter, and sent to a hospital laboratory, where either the sodium ion or chloride ion level can be measured. The accuracy of this test greatly depends on the skill of the clinician administering the collection, and the quality of the lab equipment. Furthermore, the risk of contamination is always a factor when a sample has to be transported or handled, and should be avoided if at all possible, as a false negative can be detrimental to the treatment process.

The entire collection procedure takes about an hour and requires a large sample size, for example about 50 g of sweat, which is especially difficult to collect from a newborn. The time required for the laboratory analysis is variable depending on the location of the collection and instrumentation of the lab. However, reliable sweat levels are present after five minutes. If the sodium levels in the patients sweat were read after this short five minute period, the diagnosis could be concluded hours, or even days, earlier than with the present methods. It has been shown that the sweat testing process of a suspected newborn is a time of immoderate anxiety for parents and other family members. A straightforward way of reducing stress to the family would be to promptly perform the test and obtain the results as soon as possible. Therefore, there is a need for accurate testing to be performed in real-time.

Current techniques are not adequate; analytical techniques used in ion quantification include atomic absorption spectrophotometry [AAS], inductively coupled plasma-atomic emission spectroscopy [ICP-AES], and ion chromatography, among others. Sweat conductivity tests have also been developed, but are not approved by the U.S. Food & Drug Administration [FDA], and are not expected to become diagnostic protocol. Current sensor technologies developed for ion quantification involve rigid electrodes, and/or the use of optical techniques.

Temperature detection close to the skin is normally an easily completed task using a thermometer, but it becomes more difficult when trying to detect conditions close to the skin for purposes of monitoring or controlling factors, i.e. temperature and humidity, related to the enclosed environment around the detection area. It becomes more difficult due in part to the desire for accurate measurements while maintaining comfort, especially for prolonged use or wear. The majority of temperature detectors are made from rigid materials that would create pressure points against the skin in load-bearing situations. For example, imagine temperature changes need to be detected inside the prosthetic socket of a lower limb amputee to either control a cooling system for their prosthetic or to model the patient's daily activity over a prolonged period of time. Now, the prosthetic is designed to fit snug against the patient's residual limb for proper care and usage. Having a small rigid detector constantly inside the prosthetic socket would be like walking around with a grain of sand in a shoe.

Previously, flexible temperature sensor arrays have been used to detect and record temperature through integrated circuits, which are metal thin-film interconnects and traces sandwiched between semi rigid polymer sheets. Some of the devices use a conductive polymer composite as the sensing material, while others use thin metal films in various configurations for different type of detection, i.e. temperature and strain. Others have developed temperature sensitive fibers using polymer composites or carbon nanotubes for small site and stationary electronic applications. These devices work well for electronic skins, robotics, and electronics applications, but would create pressure points and uncomfortable regions for detecting temperature changes at or close to the human dermis. A flexible temperature sensitive fabric would facilitate detecting temperature changes close to the skin for extraneous activities, or instances where pressure may be applied to the detecting surface.

The most current estimate states there are approximately 1 in 190 persons living in the United States with major limb-loss and the rate of amputations increases each year. This necessitates an importance for understanding both quality of life rated (QOLR) issues and options to remediate prevalent problems. One major issue for amputees using socket style prosthesis is the combination of heat and sweat in the socket. Most amputees wear their prosthetic for eight or more hours a day. This is troublesome for a residual limb, because the socket can become hot and humid during even just regular use and can cause a variety of dermatological conditions if proper care is not taken. The major contributors to heat and sweat inside the socket are personal activity, and socket and liner materials of construction. The materials used in socket and liner construction negatively affects the socket environment by inhibiting heat transfer away from the residual limb and just ten minutes of walking can increase the average residual limb temperature by 1.7° C. A reduction in heat transfer causes sweat inside the socket, which can create a moist, abrasive environment against the skin. Currently, there are no systems able to monitor temperature and sweat conditions at the stump-socket interface.

The present invention provides for a quantitative sodium ion sensor for use as a diagnostic tool. The present invention also fulfills the need for a soft, resistive fabric to detect temperature changes at or close to the human skin by also providing for a sensing platform able to determine temperature and sweat conditions at the stump-socket interface. Further, the present invention provides for such diagnostics and testing inexpensively, yet very accurately. The present invention provides for biosensors having wide applicability. Besides CF and stump-socket interface applications, the present invention may be advantageously used for non-limiting examples such as monitoring diabetic feet as well as military applications such as monitoring dehydration during combat or various applications to aid pilots. This device could also be extended to the diagnosis of common diabetic neurological complications, such as autonomic neuropathy or peripheral neuropathy, as these are accompanied with symptoms affecting sweat regulation.

SUMMARY OF THE INVENTION

In general, a flexible sensor for contact with skin according to the present invention includes a nanocomposite and a top layer, where the sensor provides in-situ detection in sweat or other aqueous body fluids at the skin surface of at least one physiological parameter selected from the group consisting of a physiological salt component, temperature, moisture, humidity, or combinations thereof.

In one or more embodiments, the nanocomposite of the flexible sensor further comprises a substrate and an intermediate layer.

In one or more embodiments, the substrate of the nanocomposite is non-conductive.

In one or more embodiments, the substrate is a polyamide.

In one or more embodiments, the polyamide of the substrate is nylon-6.

In one or more embodiments, the substrate is a fabric, scrim, sock, mat, scaffold, or textile.

In one or more embodiments, the substrate is formed by electrospinning.

In one or more embodiments, the intermediate layer of the nanocomposite is conductive.

In one or more embodiments, the intermediate layer is ceramic.

In one or more embodiments, the intermediate layer is carbon.

In one or more embodiments, the intermediate layer is graphene.

In one or more embodiments, the intermediate layer comprises nanoparticles, nanofibers, nanotubes, or combinations thereof.

In one or more embodiments, the intermediate layer comprises carbon nanotubes.

In one or more embodiments, the nanotubes of the intermediate layer are multi-walled carbon nanotubes (MW-CNTs).

In one or more embodiments, the intermediate layer is formed by dip-coating.

In one or more embodiments, the top layer of the flexible sensor is functionalized to detect a physiological salt component selected from the group consisting of: sodium, potassium, magnesium, calcium, chloride, hydrogen phosphate, hydrogen carbonate, and combinations thereof.

In one or more embodiments, the top layer is functionalized to detect the physiological salt component sodium to determine $Na^+$ ion concentration.

In one or more embodiments, the top layer is calixarene.

In one or more embodiments, the top layer is calix[4] arene.

In one or more embodiments, the top layer is functionalized to detect temperature, moisture, humidity, or combinations thereof.

In one or more embodiments, the top layer is polypyrrole (PPy).

In accordance with at least one aspect of the present invention, a method of fabricating a flexible sensor suitable for contact with skin includes electrospinning at least one polyamide-producing monomer to form a non-conductive polyamide substrate; attaching at least one plurality of conductive nanoscale attachments, wherein the nanoscale attachments are selected from nanotubes, nanoparticles, or combinations thereof, to form an intermediate layer; and functionalizing the intermediate layer to form a top layer.

In one or more embodiments, the method includes employing the flexible sensor as a diagnostic tool to make real-time, accurate diagnosis of cystic fibrosis and where the top layer is calix[4]arene.

In one or more embodiments, the method includes employing the flexible sensor as a socket liner to provide in-situ detection in sweat or other aqueous body fluids at the skin surface of at least one physiological parameter selected from the group consisting of a physiological salt component, temperature, moisture, humidity, or combinations thereof and where the top layer is polypyrrole (PPy).

In accordance with at least one aspect of the present invention, a device for measuring at least one physiological parameter selected from the group consisting of a physiological salt component, temperature, moisture, humidity, or combinations thereof at the surface of skin includes a fabric sensor, a controller, and an interface, wherein the fabric sensor comprises a nanocomposite and a top layer.

In one or more embodiments, the top layer of the device is calix[4]arene.

In one or more embodiments, the device is used as a tool to diagnose cystic fibrosis.

In one or more embodiments, the top layer of the device is polypyrrole (PPy).

In one or more embodiments, the device employs the fabric sensor as a sock to fit over a stump.

BRIEF DESCRIPTION OF THE DRAWINGS

For a full understanding of the invention reference should be made to the following detailed description and the accompanying drawings, wherein.

DETAILED DESCRIPTION OF THE ILLUSTRATIVE EMBODIMENTS

Embodiments of the present invention are based, at least in part, on the discovery of a sensor able to monitor parameters such as ion concentration, temperature, and humidity in-situ. In one or more embodiments, the sensor includes a substrate, an intermediate layer, and a top layer, wherein at least the top layer is functionalized to measure ion concentration, humidity, temperature, or a combination thereof; in other words, the top layer is tailored to monitor particular parameters. The substrate and intermediate layer form a nanocomposite. In particular embodiments, the sensor provides real-time analysis of sweat or other aqueous body fluids. In one or more embodiments, the sensor advantageously monitors Na+ concentration and/or moisture/humidity levels. The sensor of the present invention can be used for accurate and cost effective real-time diagnostics and therapeutics. In one or more embodiments, the sensor of the present invention provides a flexible fabric tailored to monitor temperature and other biophysical properties, providing for an easier and more comfortable way for a patient to self administer therapies or diagnostic procedures.

In the present invention, the following terms are used to describe sensors of the invention including amperometric, biosensor, and wearable sensors. Amperometric sensors measure the electric current flowing under an applied potential difference between two electrodes. Biosensors are devices that monitor and transmit information about a life process. Wearable sensors are sensors that may be worn by the users to achieve individualization of diagnostics. These terms may be used interchangeably for the purposes herein.

Cystic fibrosis (CF), a genetic disease that attacks the lungs, pancreas, liver, and intestines, is characterized by the abnormal transport of sodium and chloride ions across the epithelium and is therefore most commonly diagnosed by sweat testing. The present invention provides a flexible electronic sensor developed to quantify the amount of sodium ions in sweat in real-time, alleviating the wait time, large sample size, possible contamination, and expensive analytical equipment associated with current procedures.

In one or more embodiments, the present invention is directed to a flexible sensor suitable for contact with skin comprising: a nanocomposite and a top layer; where the sensor provides in-situ detection in sweat or other aqueous body fluids at the skin surface of at least one physiological parameter selected from the group consisting of a physiological salt component, temperature, moisture, humidity, or combinations thereof.

Figure 1:
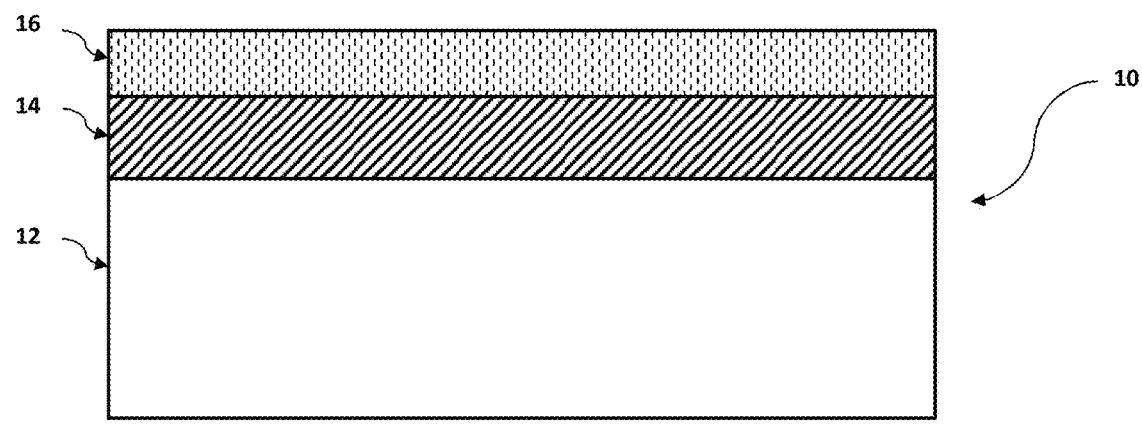
FIG. 1 is a schematic representation of sensor 10 and includes substrate 12, intermediate layer 14, and top layer 16. The substrate and intermediate layer together may also be referred to as a nanocomposite.

In one or more embodiments, the sensor of the invention is comprised of a substrate, an intermediate layer, and a top layer, wherein at least the top layer is functionalized to measure ion concentration, humidity, temperature, or a combination thereof. Referring now to FIG. 1, a sensor of the present invention, which is flexible yet conductive, is shown, generally indicated by the numeral 10. FIG. 1 is a schematic representation of sensor 10 and includes substrate 12, intermediate layer 14, and top layer 16. The substrate and intermediate layer together may also be referred to as a nanocomposite. In one or more embodiments, the flexible sensor comprises a nanocomposite and a top layer, wherein the nanocomposite further comprises a substrate and an intermediate layer.

Substrate 12 may be solid or porous. In one or more embodiments, substrate 12 is polymeric. In one or more embodiments, substrate 12 is non-conductive. In one or more embodiments, substrate 12 may be fibrous. In one or more embodiments, the substrate is a fabric, mat, scrim, scaffold, or textile. The substrate may also be referred to as an electronic fabric or a smart textile. The substrate may be made by means known by those skilled in the art. In one or more embodiments, substrate 12 is formed by electrospinning.

Any chemical resistant polymer possessing a low Young's modulus and abrasion resistance is suitable as substrate in the present invention. The material should be sufficiently tough for conducting a sweat test on either adult skin or a wriggling newborn. In one or more embodiments, the substrate is a polyamide. In one or more embodiments, the polyamide is Nylon 6.

As nylon is also used in some clothing, its spatial properties can be easily manipulated to fit the size and shape of the desired testing area. The high surface area and hydrophilicity of nylon nanofibers make it a nominal fabric for a flexible substrate. Nylon is therefore suitable in the present invention as it is possible to be made into various sizes and conformations to best fit a number of patients. This eliminates the possibility of having to restart the test due to the collection material falling off or becoming contaminated.

In one or more embodiments, the substrate may be also referred to as a fabric, scrim, sock, mat, scaffold, or textile. In at least one embodiment of the present invention, the mat or sock is comprised of a polyamide such as Nylon 6 or nylon-6, also referred to as polycaprolactam, which is a high strength polymer characterized by a high elastic modulus and good chemical and abrasion resistance. Nylon 6 is used in such materials as surgical sutures and toothbrush bristles. The flexible electrode material of the present invention may be used to determine ion concentration as well as subtle changes in temperature and humidity conditions. Nylon 6 is suitable for use in making flexible resistance temperature detectors (FRTDs).

It will be appreciated that any known monomer suitable for producing a polyamide when polymerized may be used in the present invention. In some embodiments of the present invention, the at least one polyamide-producing monomer may be selected from caprolactam, 11-amino undecanoic acid, and laurolactam so as to produce nylon 6, nylon 11 and nylon 12, respectively. In other embodiments, the at least one polyamide-producing monomers includes at least two monomers wherein hexamethylenediamine (HMD) is reacted with an acid selected from adipic acid (to produce nylon 6,6), azelaic acid (to produce nylon 6,9), sebacic acid (to produce nylon 6,10), and dodecanedioic acid (to produce nylon 6,12). In other embodiments, the polyamide-producing monomers may be made into polyamide copolymers by the addition of caprolactam (or lauralactam, where nylon 12 is desired as one of the blocks) with the hexamethylenediamine and one of the acid above. Such copolymers would include nylon 6/66 (with adipic acid), nylon 6/69 (with azelaic acid), nylon 6/610 (with sebacic acid) and nylon 6/612 (with dodecanedioic acid). In still another embodiment, caprolactam may be copolymerized with laurolactam to produce nylon 6/12. In the present invention, any diamine can essentially be added with any diacid to produce a polyamide matrix suitable for the present invention. Likewise, at least one polyamide-producing monomer can be selected from any number of diamines (typically at least one) and any number of diacids (typically at least two) sufficient to produce a polyamide copolymer. In one embodiment, the at least one polyamide-producing monomer is caprolactam.

In one or more embodiments, the substrate is Nylon-6 wherein the Nylon-6 is characterized by a molecular weight of 9 or more kg/mol to 11 or less kg/mol. In a specific embodiment, the viscosity average molecular weight is about 10 kg/mol.

The non-conductive polymer substrate of the invention is functionalized to form intermediate layer 14, where the intermediate layer is conductive. Intermediate layer 14 may be solid or porous. Intermediate layer 14 may be organic or inorganic. In one or more embodiments, intermediate layer 14 is ceramic. In one or more embodiments, intermediate layer 14 is carbon. In one or more embodiments, intermediate layer 14 is comprised of graphene. Graphene is the basic structural element of some carbon allotropes including graphite, charcoal, carbon nanotubes and fullerenes.

In one or more embodiments, intermediate layer 14 comprises nanoparticles, nanofibers, nanotubes, or combinations thereof. In one or more embodiments, the substrate or non-conductive polymer is functionalized with highly-conductive carbon nanotubes (CNTs) to allow for enhanced charge carrier transport to the electrodes. In same or other embodiments, intermediate layer 14 of the flexible sensor of the invention comprises multi-walled carbon nanotubes (MWNT or MWCNT).

MWCNTs are a plurality of single-wall carbon nanotubes, of varying diameters, that are coaxially arranged with an intertube separation of approximately 0.34 to 0.35 nm. This is similar to the interplane separation in graphite. Multi-walled nanotubes (MWCNT) may consist of multiple rolled layers (concentric tubes) of graphene.

Carbon nanotube functionalization is suitable for sensors of the present invention due to their excellent mechanical and thermal stability, high thermal and electrical conductivity, and large specific area. Depending on the type of sensor, carbon nanotubes may be tailored to sense an array of physical properties, for example biological, chemical, flow, gas, mass, optical, position, pressure, stress, strain, and thermal phenomena.

As known by those skilled in the art, various techniques may be used to provide the carbon nanotube functionalized nylon-6 matrix. These techniques include, but are not limited to, (a) electro polymerization techniques, (b) wet chemistry, (c) dip coating, (d) chemical vapor deposition, (e) plasma deposition, (f) atomic layer deposition, (g) physical vapor deposition, (h) controlled environment heating, or (i) a combination thereof.

Attachment of the carbon nanotubes onto the substrate to form a nanocomposite is maintained by non-covalent bonding.

In at least one specific embodiment, the flexible sensor of the invention includes an intermediate layer, where the intermediate layer is formed by dip-coating. Dip-coating is done by carefully dipping the electrospun nylon-6 mat into a specific concentration of surfactant-stabilized MWNTs for a specified amount of time.

In at least one specific embodiment, the flexible sensor of the invention includes an intermediate layer, where the intermediate layer is formed by vacuum filtration. Vacuum filtration is completed by filtering MWCNTs from a solution containing 25 or more mg/L MWCNTs to 250 or less mg/L MWCNTs at a vacuum level of 2 or more in Hg to 25 or less in Hg to form a layer of MWCNTs on top of the nylon 6 substrate.

In at least one specific embodiment, a nylon-6/MWCNT nanocomposite material has a higher tensile strength (+25%), lower strain at break (−18%), higher yield stress (+34%), higher Young's modulus (~28 MPa) than nylon-6 alone when the nanotubes are electrospun into the material. The material is also abrasion and chemical resistant, has spatial properties that are easy to manipulate, large surface area per mass, and is highly permeable.

The nanocomposite including substrate 12 and intermediate layer 14 is then functionalized to form a top layer 16 thereon, where the top layer is functionalized to detect a physiological salt component selected from the group consisting of: sodium, potassium, magnesium, calcium, chloride, hydrogen phosphate, hydrogen carbonate, and combinations thereof. In same or other embodiments, the flexible sensor includes a top layer, where the top layer is functionalized to detect temperature, moisture, humidity, or combinations thereof.

In one or more embodiments, the flexible sensor of the present invention is a diagnostic tool to measure, monitor, or detect in aqueous body fluids at the skin surface at least one physiological parameter selected from the group consisting of a physiological salt component, temperature, moisture, humidity, or combinations. Functionalization of the nanocomposite to form top layer 16 includes tailoring the top layer to measure for one or more specific parameters. In one or more embodiments, the nanocomposite including substrate 12 and intermediate layer 14 is functionalized with one or more top layers adjacent to each other to provide for measuring for one or more specific parameters. In same or other embodiments, the flexible sensor of the invention measures, monitors, or detects multiple parameters parameter selected from the group consisting of a physiological salt component, temperature, moisture, humidity, or combinations.

In one or more embodiments, the top layer 16 is a cyclic oligomer. Attachment of the top layer to the intermediate layer comprising carbon nanotubes is maintained by covalent bonding.

In one or more embodiments, the flexible sensor of the invention includes a top layer, where the top layer is functionalized to detect the physiological salt component sodium to determine $Na^+$ ion concentration. In other words, a top layer 16 provides functionalization to detect ion concentration. In same or other embodiments, top layer 16 provides functionalization to detect sodium ion concentration or $Na^+$ concentration, also referred to as $[Na^+]$.

In one or more embodiments, the top layer 16 forms a supramolecular complex in the presence of ions. In one or more embodiments, top layer 16 is a cyclo-oligomeric calixarene, which has been shown to selectively form a supramolecular complex with sodium ions. A calixarene is a macrocycle or cyclic oligomer based on a hydroxyalkylation product of a phenol and an aldehyde. Calixarene nomenclature is straightforward and involves counting the number of repeating units in the ring and include it in the name. A calix[4]arene has 4 units in the ring and a calix[6]arene has 6.

In one or more embodiments, the flexible sensor of the invention includes a top layer, where the top layer is calixarene. In same or other embodiments, the top layer is calix[4]arene. In one or more embodiments, upon supramolecular complex formation, the charge carriers are drawn away from the carbon layer, hence the current is impeded, and the sodium ion detection is prevalent at levels appropriate for accurate diagnosis of CF.

Figure 2A:
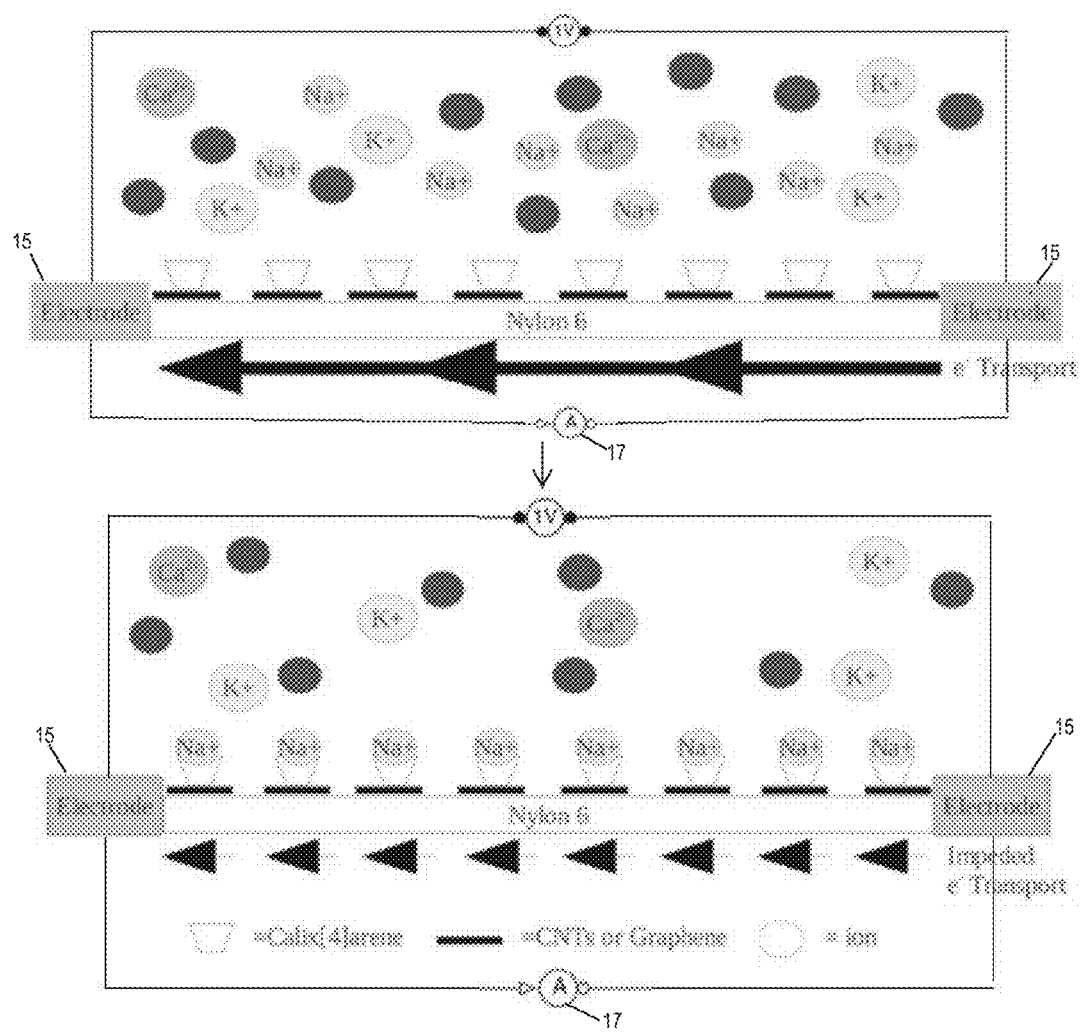
FIG. 2A is a schematic drawing depicting the selective binding of sodium ions onto the nylon-6/MWCNT/calixarene sensor causing impeded charge carrier mobility and FIG. 2B is a schematic drawing depicting the electron-flow increases across the FRTD surface as heat and humidity increases.

In some embodiments, the fabric sensor is employed to measure, monitor, or detect sodium ion concentration. FIG. 2A is a schematic drawing depicting at least one embodiment of the invention. The flexible sensor of the present invention is also capable of detecting a change in sodium ion concentration and may also be referred to as a 'flexible electrode' or 'sweat electrode' or 'sweat detector'. As previously described, Nylon 6 is a non-conductive polymer that may be functionalized with conductive carbon nanotubes (CNTs) or graphene to form an intermediate layer. CNTs have both been found to exhibit superb thermal and electrical conductivities, as well as high strength and stiffness. For selective determination of sodium ion content, the intermediate layer is functionalized with a cyclo-oligomeric calix[4]arene to form a top layer, which has been shown to form a supramolecular complex with sodium ions. Upon complex formation with the sodium analyte, the current will be impeded and the ion detection will be prevalent, as illustrated in FIG. 2A.

A device according to the present invention includes a fabric sensor, as depicted in FIG. 2A, further comprising electrodes (shown). A device according to the present invention provides for measuring, monitoring, or detection of at least one physiological parameter selected from the group consisting of a physiological salt component, temperature, moisture, humidity, or combinations thereof at the surface of skin, wherein the device comprises: a fabric sensor, a controller, and an interface, wherein the fabric sensor comprises a nanocomposite and a top layer. In one or more embodiments, the device is employed to measure, monitor, or detect sodium ion concentration. In one or more embodiments, the top layer is calix[4]arene. In same or other embodiments, the device is used as a tool to diagnose cystic fibrosis.

A device according to the present invention further comprises (not shown) a basic unit as known in the art to communicate with the electrodes 15. The basic unit comprises a controller 17 to interpret output or signal(s) from the sensor. The signal output from the sensor to detect sodium ion concentration, as in the embodiment depicted in FIG. 2A, is current; however, the output may more generally include voltage, current, pulse, waveforms, or other signals, or combinations as appropriate to the particular sensor. The basic unit further comprises an interface coupled to the controller 17 to provide data to the user, as is known by those skilled in the art.

In one or more embodiments, the top layer 16 is polymeric. Attachment of the top layer to the intermediate layer comprising carbon nanotubes is maintained by noncovalent Van der Waals forces, and more specifically Debye forces due to inherent dipoles in the nylon 6 polymer chain resulting from repeating monomeric units, each of which contain a double bonded oxygen and secondary amine group, which induces dipoles in the carbon nanotube frameworks as the nanotubes get to within approximately four angstroms in distance from the nylon nanofiber surfaces.

In one or more embodiments, a top layer 16 provides functionalization to detect temperature and humidity variations or fluctuations. In one or more embodiments, top layer 16 is polypyrrole (PPy), which is a conductive polymer that has been shown to respond to temperature and humidity variations, as well as a range of different gases at various temperatures. Polypyrrole is a chemical compound formed from a number of connected pyrrole ring structures. Polypyrroles are also referred to as pyrrole blacks or polypyrrole blacks. Polypyrrole is fairly stable, but when exposed to the ambient environmental conditions of air and moisture, degrades by oxidative processes.

Figure 2B:
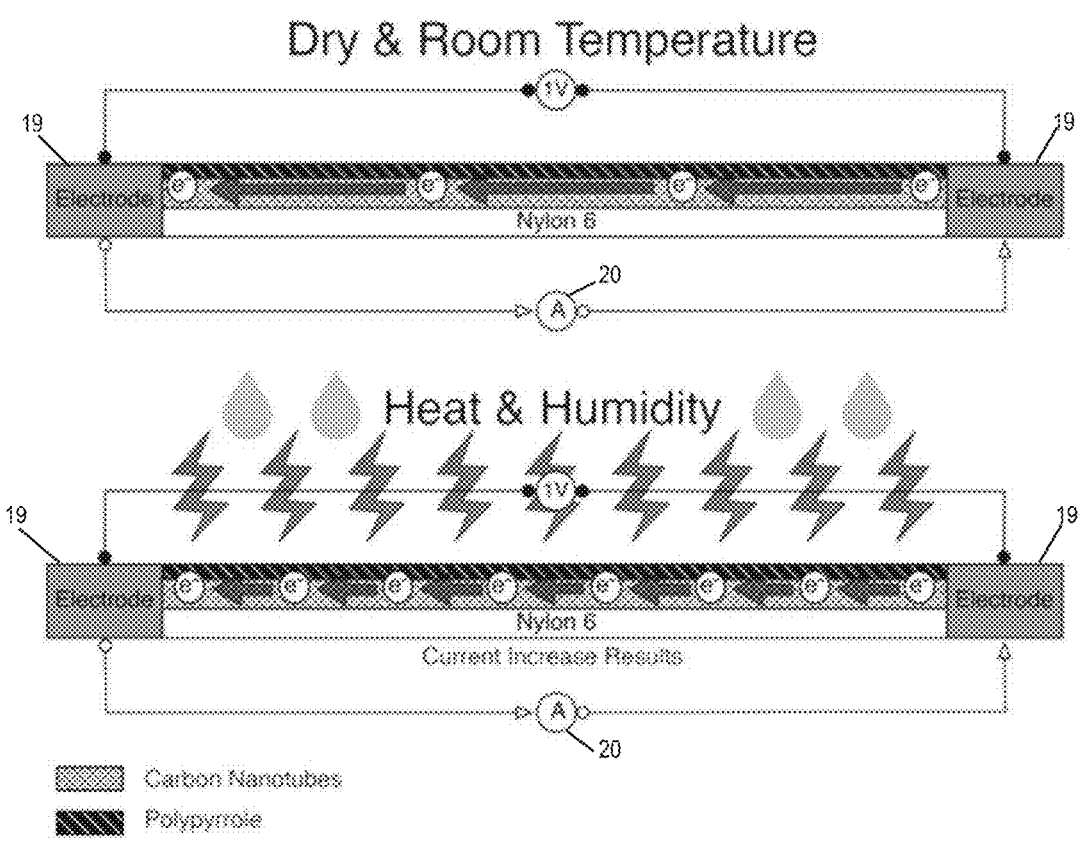

FRTDs as in at least one embodiment of the present invention detect temperature changes from about 25° C. to about 45° C. FIG. 2B shows a schematic depicting at least one embodiment of the invention. FIG. 2B illustrates how electron-flow increases across the detector surface as heat and humidity increases allowing more electron flow across its surface as temperature and humidity increase. This material could be used to monitor the relative environment in non-limiting examples such as prosthetic sockets and smart clothing. A nanocomposite constructed of an otherwise nonconductive polymer, nylon-6, and functionalized with conductive MWCNTs and PPy can act as a temperature and humidity-sensing resistor.

A device according to the present invention includes a fabric sensor, as depicted in FIG. 2B, further comprising electrodes (shown). A device according to the present invention provides for measuring, monitoring, or detection of at least one physiological parameter selected from the group consisting of a physiological salt component, temperature, moisture, humidity, or combinations thereof at the surface of skin, wherein the device comprises: a fabric sensor, a controller, and an interface, wherein the fabric sensor comprises a nanocomposite and a top layer. In one or more embodiments, the device is employed to measure, monitor, or detect temperature or humidity. In one or more embodiments, the top layer is polypyrrole (PPy). In same or other embodiments, the fabric sensor of the device is a sock to fit over a stump.

A device according to the present invention further comprises (not shown) a basic unit as known in the art to communicate with the electrodes 19. The basic unit comprises a controller 20 to interpret output or signal(s) from the sensor. The signal output from the sensor to detect changes in heat and humidity, as in the embodiment depicted in FIG. 2B, is current; however, the output may more generally include voltage, current, pulse, waveforms, or other signals, or combinations as appropriate to the particular sensor. The basic unit further comprises an interface coupled to the controller 20 to provide data to the user, as is known by those skilled in the art.

A flexible device such as described herein may be integrated with a flexible cooling system to provide "smart" cooling of a prosthetic socket. In addition, the FRTD of the present invention may also be used in a host of other applications such as for the military, diagnostics and therapeutics, or industries where exposure to elevated temperatures is high and there is a need for cooling systems in clothing. A device according to the present invention is useful for biomedical and electronics applications as well, wherein it is possible to functionalize carbon nanotubes with different materials to detect a whole range of specific biological and chemical analytes.

In at least one aspect of the invention, the a method of fabricating a flexible sensor suitable for contact with skin is provided comprising: electrospinning at least one polyamide-producing monomer to form a non-conductive polyamide substrate; attaching at least one plurality of conductive nanoscale attachments, wherein the nanoscale attachments are selected from nanotubes, nanoparticles, or combinations thereof, to form an intermediate layer; and functionalizing the intermediate layer to form a top layer.

In one or more embodiments, the method of the invention includes a flexible sensor, where the flexible sensor is employed as a diagnostic tool to make real-time, accurate diagnosis of cystic fibrosis and where the top layer is calix[4]arene.

In same or other embodiments, the method of the invention includes a flexible sensor, where the flexible sensor is a socket liner to provide in-situ detection in sweat or other aqueous body fluids at the skin surface of at least one physiological parameter selected from the group consisting of a physiological salt component, temperature, moisture, humidity, or combinations thereof and where the top layer is polypyrrole (PPy).

Properties of the sensor such as nylon properties, nanotube functionalization, calixarene or PPy loading, etc. are optimized in order to create a more sensitive and robust electrode. In one or more embodiments of the present invention, a flexible electronic sensor able to quantify the amount of sodium ions in sweat alleviating the wait time, family anxiety, expensive equipment, personnel, and large sample size currently associated with sweat testing is provided. In one or more embodiments, an integrated sensor of the present invention provides for detection of ion concentration, temperature, humidity, and combinations thereof.

Figure 3:
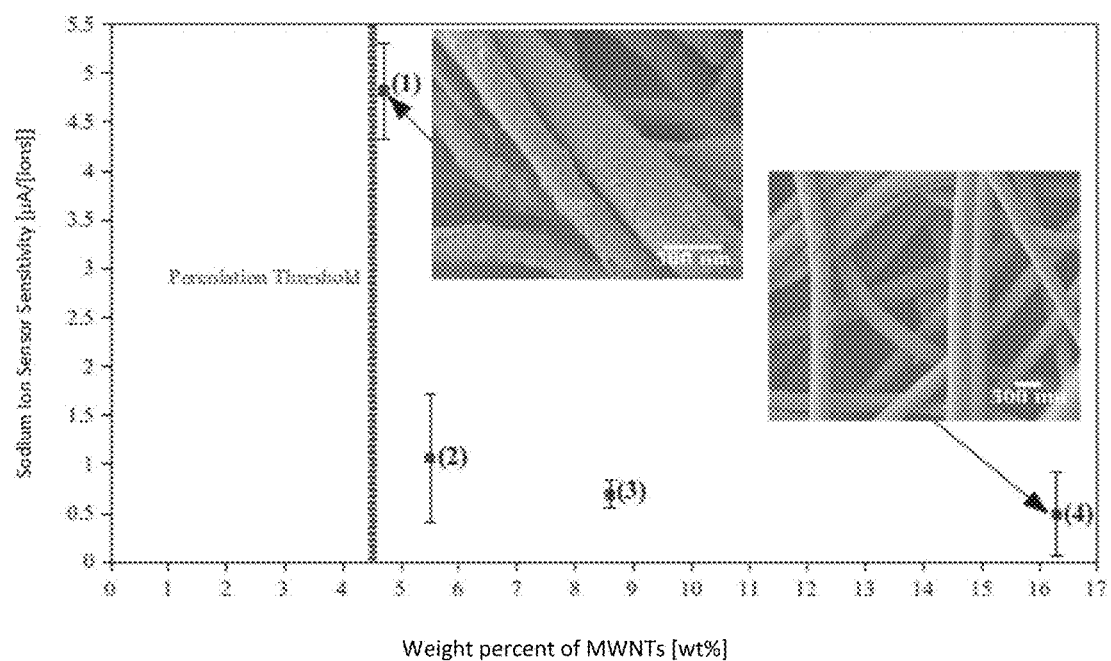
FIG. 3 is a graph showing how the sensors' sensitivity changes as weight percent of MWCNTs is varied; the inset SEM micrographs show the surface of the optimized (low wt % MWCNT) sensor and the high wt % MWCNT sensor.

The range of loading of carbon nanotubes onto the substrate is from 0.25 g/L in solution (Triton X-100 or Triton X-114) or more to 2.50 g/L in solution (Triton X-100 or Triton X-114) or less. Optimized loadings of CNT's are illustrated in FIG. 3. FIG. 3 shows how the sensors' sensitivity changes as weight percent of CNTs is varied; the inset SEM micrographs show the surface of the optimized (low wt % MWCNT) sensor and the high wt % MWCNT sensor. Table 1 shows the average responses and sensitivities of various sensor fabrication schemes.

TABLE 1

| Sample | Average Response [µA] | Average Sensitivity [µA/[ions]] |
|---|---|---|
| MWCNT (0.25 g/L) in Triton X-100 | 90.71 ± 16 | 4.82 ± 0.49 |
| MWCNT (0.25 g/L) in Triton X-114 | 31.91 ± 18 | 1.06 ± 0.65 |
| MWCNT (2.5 g/L) in Triton X-100 | 11.49 ± 20 | 0.70 ± 0.14 |
| MWCNT (2.5 g/L) in Triton X-114 | 12.47 ± 12 | 0.49 ± 0.43 |

In a specific embodiment, nylon-6/MWCNT/calixarene nanocomposites can be effectively used for selective and sensitive sodium ion detection in liquids, particularly sweat samples. In at least one preferred embodiment, the optimized sensor fabrication scheme has been shown to be the MWCNTs (0.25 g/L) dispersed in 0.3 wt % Triton® X-100 in water. This sensor's selectivity to sodium ions, due to its calix[4]arene-functionalized surface, separates it from a simple sweat conductivity sensor, which is not permitted for diagnosis of CF in the United States. AC measurement techniques can also be implemented to eliminate the charging affects of the interfering ions, hence, eliminating the blocking of sodium ions from forming a supramolecular complex with the calixarene molecules. Sensors of the present invention may be also adapted to the diagnosis of common neuropathies caused by both Type-I and Type-II diabetes.

In one or more embodiments herein, the polyamide forming the substrate is nylon-6. In other embodiments herein, the nylon-6 is from about 9 to about 11 kg/mol. In one or more embodiments, nylon-6 is at least 9.8 kg/mol. In other embodiments, nylon-6 is at least 10 kg/mol.

In other or the same embodiments herein, the loading of CNTs onto the substrate to form the nanocomposite is characterized in weight percent CNTs per total weight of nanocomposite. In one or more embodiments, the loading of CNTs is from about 2 or more wt. % to about 10 or less wt. %. In other embodiments, the loading of CNTs is from about 2 or more wt. % to about 8 or less wt. %. In other or the same embodiments herein, the loading of CNTs is at least 4 wt. % and at most 6 wt. %. In at least one embodiment, the loading of CNTs is at least 2 wt. %. In yet another embodiments, the loading of CNTs is at least 4 wt. %.

In one or more embodiments, the CNTs may be characterized by an average diameter size (in nm) of from about 1 or more nm to about 100 or less nm. In other or the same embodiments, the CNTs may be characterized by an average diameter size of from about 10 or more nm to about 20 or less nm. In one or more embodiments, the CNTs may be characterized by an average length (in μm) of from about 0.1 or more μm to about 10 or less μm. In other or the same embodiments, the CNTs may be characterized by an average length of from about 0.5 or more μm about 2 or less μm.

In one or more embodiments, the top layer is polymeric. In other or the same embodiments, the top layer is calixarene. In other or the same embodiments herein, the loading or concentration of calixarene in toluene onto the nanocomposite to form the sensor is from about 0.5 or more mg/mL to about 5 or less mg/mL. In other or the same embodiments, the loading of calixarene is from about 1 or more mg/mL to about 4 or less mg/mL. In other or the same embodiments, the loading of calixarene is from about 2 or more mg/mL to about 3 or less mg/mL. In other or the same embodiments, the loading of calixarene is about 2.5 or more mg/mL. In other or the same embodiments, the loading of calixarene is at least 0.5 mg/mL, in other embodiments at least 1.0 mg/mL, in other embodiments at least 1.5 mg/mL, in other embodiments at least 2.0 mg/mL, and in other embodiments at least 2.5 mg/mL. In other or the same embodiments, the loading of calixarene is at most 4.0 mg/mL, in other embodiments at most 3.5 mg/mL, in other embodiments at most 3.0 mg/mL, and in other embodiments at most 2.5 mg/mL.

In other or the same embodiments, the top layer is a conductive polymer. In one or more embodiments the top layer is polypyrrole. In one or more embodiments, the top layer is formed by vapor phase polymerization of pyrole. In other or the same embodiments herein, the loading or concentration to be polymerized to form polypyrrole onto the nanocomposite to provide the sensor is from about 10 to about 200 mmol $FeCl_3$ adsorbed onto the nanocomposite. In other or the same embodiments, the loading is from about 50 to about 150 mmol $FeCl_3$ adsorbed. In other or the same embodiments, the loading is from about 75 to about 125 mmol $FeCl_3$ adsorbed. In other or the same embodiments, the loading is about 100 mmol $FeCl_3$ adsorbed. The length of polymerization time is between about 1 and about 4 days. In a specific embodiment, the length of polymerization is 2 or more days.

Various modifications and alterations that do not depart from the scope and spirit of this invention will become apparent to those skilled in the art. This invention is not to be duly limited to the illustrative embodiments set forth herein.

EXAMPLES

Example 1

Ion Sensor

In a non-limiting example of the present invention, an optimized sensor is fabricated using nylon-6 dip-coated in MWCNTs in water (stabilized using a TX-100 surfactant) and then dip-coated in p-tert-butyl-calix[4]arene dissolved in toluene.

Chemicals

The nylon-6 [poly(caprolactam)] (Scientific Polymer Products, Inc., viscosity average MW—10,000, pellets), multi-walled carbon nanotubes [MWCNTs] (Nanostructured & Amorphous Materials, Inc., 10-20 nm diameter, 0.5-2 μm length, 200 m$^2$/g), p-tert-butyl-calix[4]arene (Aldrich), acetic acid (Sigma-Aldrich, ≥99%), formic acid (Fluka Analytical, puriss, ~98%), Triton® X-100 (Sigma), and Triton® X-114 (Acros Organics) were used as purchased.

Sensor Fabrication

Nylon-6 nanofiber (NF) mats were electrospun using a 14 wt % nylon-6 in formic acid/acetone (1:1 wt %) at a rate of 9.1 μL/min. The electrospinning conditions (30 kV voltage and 8 cm needle-collector distance) were implemented for a four hour block on a rotating drum electrode. To functionalize the electrospun nylon-6 mat with MWCNTs, a dip-coating procedure was used. In this procedure, the nylon-6 mats are simply dipped into a specific concentration of MWCNTs in 0.3 wt % Triton X-100 surfactant in $H_2O$, or 0.3 wt % Triton X-114 surfactant in $H_2O$, for 30 seconds. These are carefully removed and placed in a room-temperature deionized water bath for 30 seconds, to remove excess non-adsorbed nanotubes. The mats are then left to dry under ambient conditions. The calix[4]arene functionalization was also achieved through a dip coating procedure. The MWCNT/nylon-6 NF mats were sonicated for 5 minutes in a 2.5 mg/mL p-tert-butyl-calix[4]arene in toluene, then left overnight to react. The MWCNT/calixarene-functionalized nylon-6 NF mats were then dried under ambient conditions overnight and used for further experimentation.

Electrochemical Analysis

Figure 4:
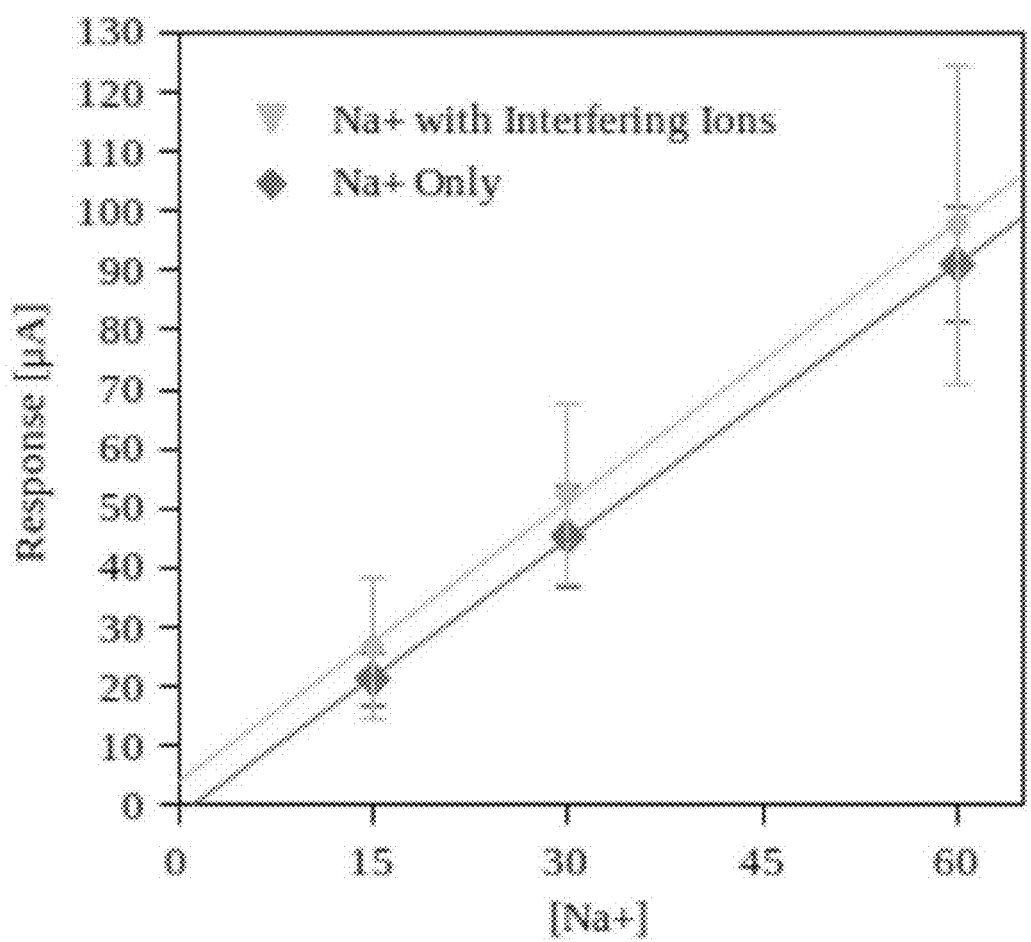
FIG. 4 shows calibration curves showing the sensor's response and standard deviation varying sodium ion concentration with and without various concentrations of interfering ions.

Electrochemical analyses were performed on a Gamry Instruments Reference 3000 Potentiostat/Galvanostat/ZRA via direct-current (DC) amperometry at a voltage of 0.88 volts. The fabricated sensor was placed on a glass slide and clipped down with two micro-alligator clips [Nickel-plated steel] (one on each end of the 1 cm×1 cm sensor). A two electrode setup was used, as drops (10 μL) of DI-water and 15 mM NaCl were applied to the sensor. For selectivity testing, a NaCl/KCl/$CaCl_2$ synthetic sweat sample was used with concentrations of the salts being 30 mM/5 mM/0.4 mM, respectively. The responses were then measured and compared. All neat nylon-6 samples and functionalized sensor mats were taken from the same electrospun sample for comparable results. FIG. 4 includes calibration curves showing the sensor's response and standard deviation for varying sodium ion concentrations with and without various concentrations of interfering ions.

Thermal Gravimetric Analysis

All Thermal Gravimetric Analysis (TGA) was performed on a TA Instruments Q500 Thermogravimetric Analyzer, where the mats were placed in the platinum boat and a ramp of 10° C./min was employed up to 600° C. under nitrogen. All neat and MWCNT-functionalized nylon-6 mats were taken from the same electrospun sample for comparable results.

Figure 5:
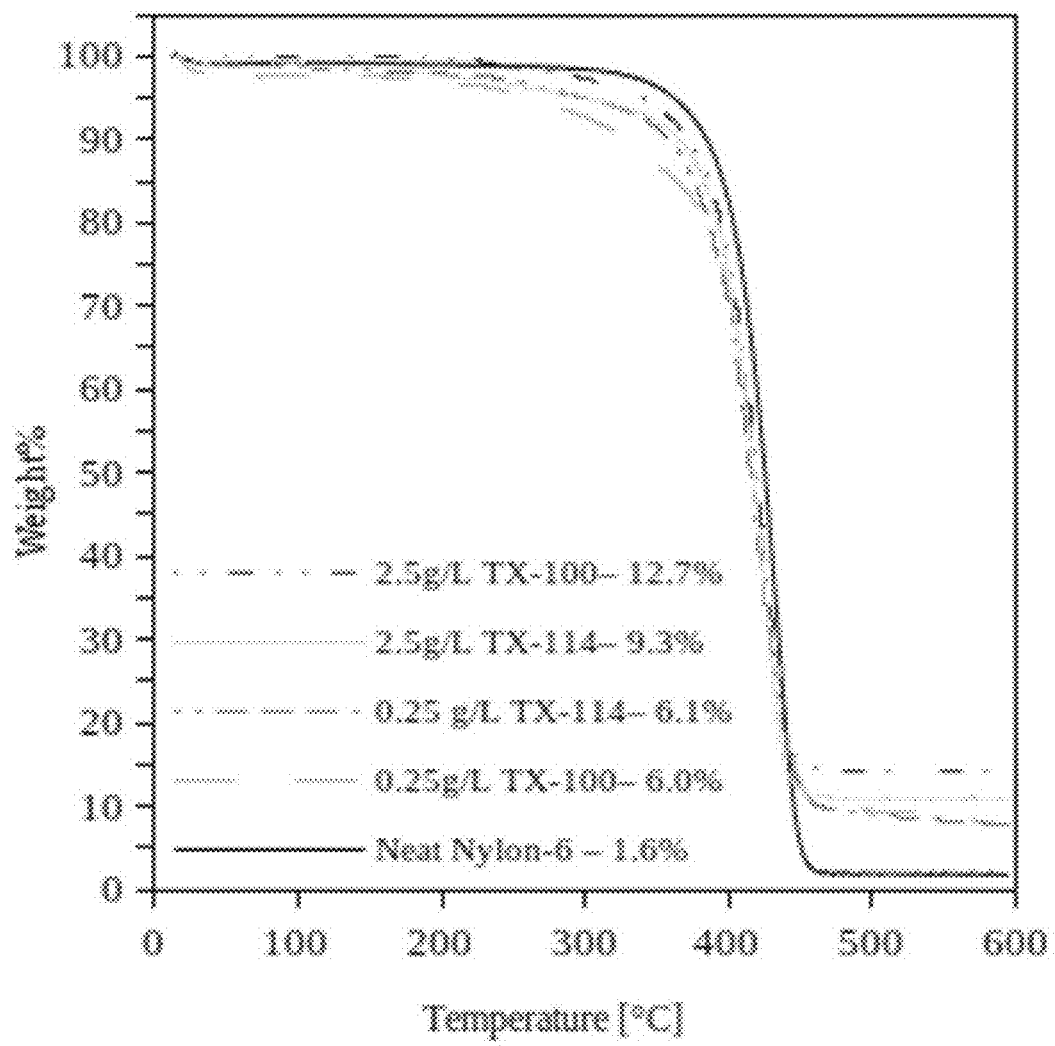
FIG. 5 shows typical TGA thermograms of MWCNT/nylon-6 nanocomposites under various dip-coating conditions [H=high concentration (2.5 g/L), L=low concentration (0.25 g/L), TX-1XX=Triton X®-100 or 114 surfactant].

Thermal gravimetric analysis (TGA) was performed for all four sensor platforms, as well as neat nylon-6 samples to examine the amount of MWCNTs adsorbed onto the surface of the nylon nanofibers. The sensors dip-coated in the higher concentrations of MWCNTs showed a higher weight percent of carbon, as seen in FIG. 5. This figure shows typical TGA thermograms of MWCNT/nylon-6 nanocomposites under various dip-coating conditions [H-high concentration (2.5 g/L), L=low concentration (0.25 g/L), TX-1XX=Triton X®-100 or 114 surfactant]. The figure shows a characteristic value for the neat nylon samples and normalized (neat nylon baseline subtracted out) values of samples prepared with various procedures. These thermograms illustrate that the TX-100 surfactant-stabilized nanocomposites showed a higher weight percent of MWCNTs adsorbed to the nylon surface, using the same weight percent of surfactant, at the high concentration of MWCNTs (2.5 g/L). Without being bound by theory, one may infer that this is due to the TX-100 surfactant more efficiently dispersing the MWCNTs onto the nylon NF surface and therefore being able to achieve a higher loading. Judging by the similar values for the nanocomposites with the low concentration of MWCNTs (0.25 g/L), these samples seemed to be limited by the amount of MWCNTs and not by the efficiency of surfactant dispersion.

Sensor Evaluation

Figure 6:
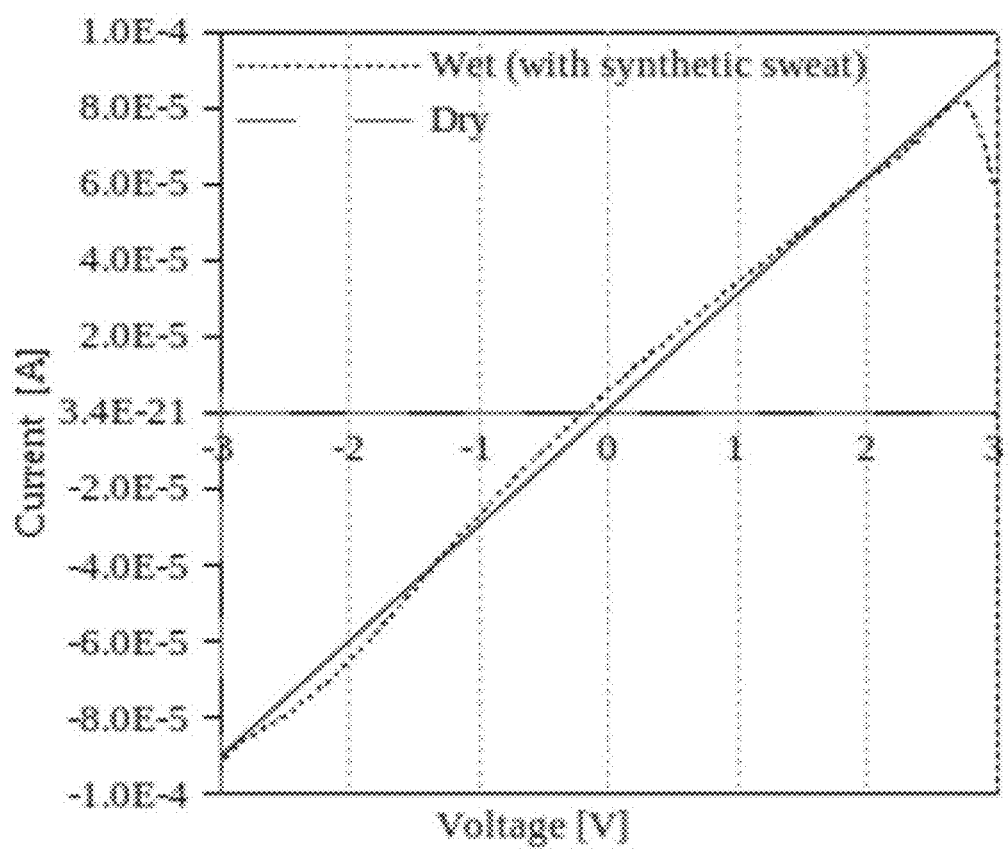
FIG. 6 is an I-V characteristic curve for the dry and wetted (with synthetic sweat) sensor.

Current-voltage (I-V) characteristic curves can be seen in FIG. 6, for both the dry and wet sensor. The wet sensor is wetted with synthetic sweat (0.4 mM $CaCl_2$, 5 mM KCl, 30 mM NaCl). The sensor becomes more conductive upon wetting. A trend line has been drawn through the wet sensor curve to show its non-linear nature. Without being bound by theory, this nonlinearity is believed to be due to ion interference effects in the electrolyte solution.

Referring again to FIG. 3, FIG. 3A shows the sensitivity of the sensor is greatly dependent on the loading of MWCNTs. The superior sensitivity of the optimized sensor [MWCNTs (0.25 g/L) in TX-100 in B)] therefore is likely attributed to the enhanced dispersion of the MWCNTs on the surface of the nylon-6 NFs, as can be seen in the SEM micrographs inset. As the weight percent of MWCNTs increased, agglomeration was observed, leading to poor dispersion and contrasting NF areas of very dense and very sparse MWCNTs. The percolation threshold of sensitivity for these nanocomposites is believed to occur at around four weight percent MWCNTs. This can be seen in FIG. 3A where the optimized sensor is seen slightly above the percolation threshold. Below this value the conductivity is too low to monitor the sensor response, and there is a sharp increase in conductivity once the weight percent of MWCNTs is increased much past said threshold. As the weight percent of the MWCNTs on the surface increases, the sensitivity of the sensor decreases. This is due to the increased number of interconnected conductive pathways that must be inhibited by the sodium-calixarene supramolecular complex in order to see a change in current. Controlling the density of CNTs on the sensing material is believed to be important in fine-tuning the performance and sensitivity of a sensor.

Figure 7:
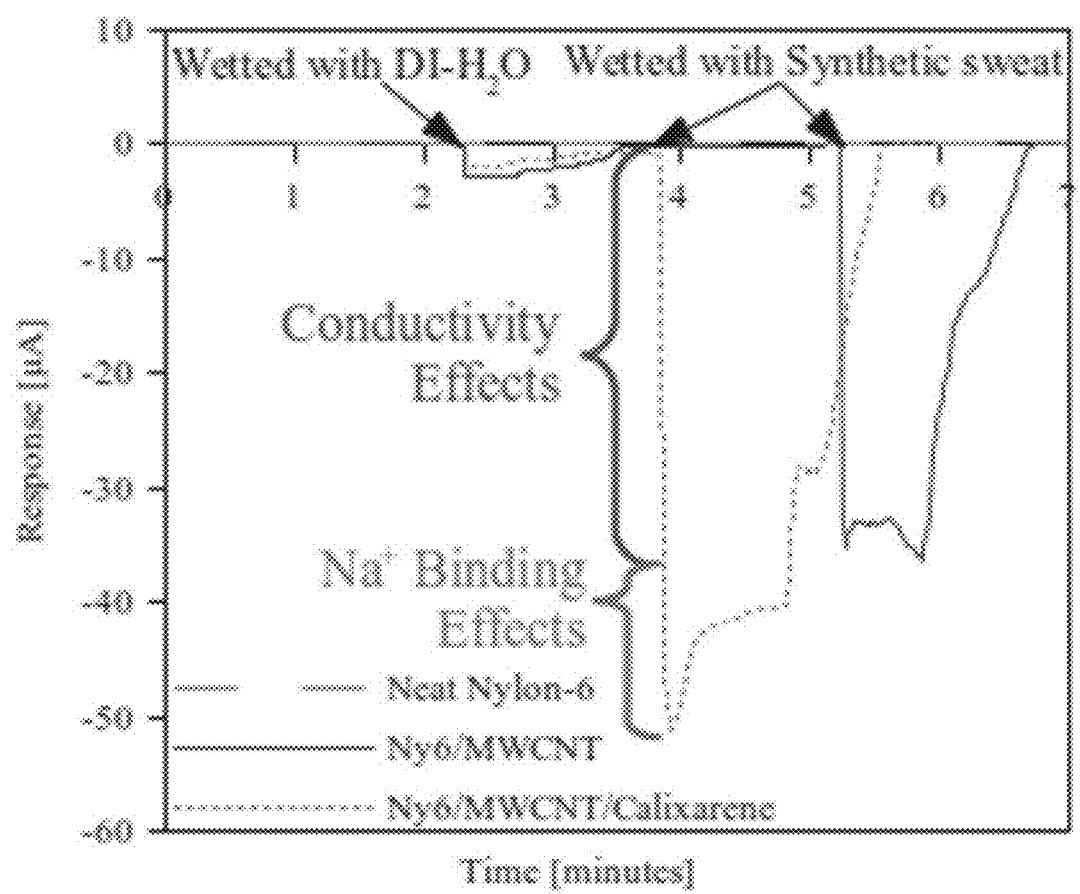
FIG. 7 is an amperometric response graph over time showing the nanocomposite's and sensor's response to synthetic sweat [0.4 mM $CaCl_2$, 5 mM KCl, 30 mM NaCl].

Calix[4]arene is a net negatively charged molecule, allowing anions to be naturally repulsed from its chalice-like feature. Size exclusion also plays a large role in the selectivity of the calixarene molecule's binding, as it has been shown previously that a number of ions present in sweat ($Li^+$, $Mg^{2+}$, $Ca^{2+}$, $Fe^{3+}$, and $Co^{2+}$ ions; some only in trace amounts) do not bind to the calix[4]arene molecule. A plot of the optimized sensor's selectivity to sodium ions in synthetic sweat, can be seen in FIG. 7. FIG. 7 shows the amperometric response graph over time showing the nanocomposite's and sensor's response to synthetic sweat [0.4 mM $CaCl_2$, 5 mM KCl, 30 mM NaCl]. In the presence of sodium, the selectivity of the calixarene molecule to sodium ions enhances the response of the sensor. The response of the nylon-6/MWCNT nanocomposite is likely due to the conductivity of the liquid, suggesting that the other ions do not readily affect the response of the sensor. The effects of conductivity can be easily subtracted out to obtain a true correlated value for the quantification of sodium ions. It can also be seen that the MWCNT/calixarene-functionalized nanocomposite shows a better response for sodium ions than the MWCNT-functionalized nanocomposite. This can be explained by the affinity of the sodium ions to the calixarene molecule, and the impedance this complex formation induces across the sensor. This allows the supramolecular complex between the sodium ions and calixarene molecules to be formed and the current to be impeded as anticipated.

Example 2

FRTD

In a non-limiting example of the present invention, an optimized FRTD sensor is fabricated by electrospinning nylon-6 as a membrane style substrate, vacuum filtration of MWCNTs onto the nylon scaffold, and vapor phase polymerization of pyrrole to PPy onto the MWCNT functionalized nylon nanofibers.

Chemicals

All chemicals and materials were used as received with no further purification. Nylon-6 with a viscosity-averaged molecular weight of 10,000 grams per mole was acquired from Scientific Polymers Inc. (U.S.A.). MWCNTs with diameters in the range of 10 to 20-nanometers and 0.5 to 2-micrometers in length were obtained from Nanostructured and Amorphous Materials Inc. (U.S.A.). Triton X-114 (TX-114) surfactant is from Acros Organics (U.S.A.) and iron chloride hexahydrate is from Flynn Scientific Inc. (U.S.A.). Pyrrole (≥99%, extra pure), formic acid (98%), and acetic acid (≥99%) were acquired through Sigma Aldrich (U.S.A.).

Electrospinning

The nylon-6 substrate was electrospun using a homemade cabinet with rotating drum. A World Precision Instruments Inc. (U.S.A.) SP101I syringe pump and a Gamma High Voltage Research (U.S.A.) ES30P-5 W voltage source were used. The fibers were spun using a 14% by weight solution of nylon-6 in a 1:1 by weight mixture of formic and acetic acid. The syringe pump flow rate was 9.1-microliters per minute. 20 to 30-kilovolts were applied between the needle and collector. The needle to collector distance was 8 to 11-centimeters. The collector was a copper sheet encased in a paper towel. It was attached to the rotating drum, which was powered by variac at a setting of 30-volts to give approximately 7-revolutions per minute. The fiber mats were spun for 4 or 8-hours for varying mat thicknesses.

Nylon-6 Functionalization

The nylon-6 fiber mat was cut into multiple 47-millimeter diameter discs for use as membrane style filters. Each membrane was placed into a Fisherbrand® membrane vacuum filtration funnel. Then it was wet with approximately 1-milliliter of 1% TX-114 solution. A 1-gram per liter MWCNT solution was made in 1% TX-114 and diluted to desired MWCNT concentrations for filtration because of the enhanced absorption efficiency of TX-114 for MWCNTs. 7.5 milliliters of this solution filtered through the nylon-6 membranes using approximately 17-kilopascals of vacuum. The membranes were washed with deionized water and acetone and allowed to dry before application of 100-millimolar iron chloride hexahydrate solution. The iron chloride solution gravity filtered through the membrane and it dried overnight in a desiccator. The membranes placed into the polymerization chamber with 1 to 2-milliliters of pyrrole sitting next to it in a beaker had approximately 100-kilopascals of vacuum applied to facilitate pyrrole vaporization. The composite was allowed to sit for 48 hours in the pyrrole vapor. After polymerization of pyrrole to polypyrrole, the detectors were allowed to sit covered, in air until testing.

Detector Testing and Characterization

Resistance temperature detection is a highly utilized natural material property in which a change in temperature is proportionally correlated to a temperature dependent change in resistance of the detector material and has become widely utilized for laboratory and everyday temperature measurement applications. Equation 1 is the mathematical model, which describes resistance temperature detection. The equation shows the experimentally determined TCR, or $\alpha$, which is a proportionality constant that is unique and constant for a material that acts as a resistor. This parameter emphasizes the linear relationship between a material's changes in resistance with changes in temperature.

$$\alpha = \frac{\Delta R}{\Delta T}\left(\frac{1}{R_0}\right) \quad (1)$$

In order to calculate the resistance, R, of a material, Equation 2, or Ohm's law is employed where V and I represent the applied voltage and measured current, respectively. RTDs are most commonly made from pure metals in the form of encapsulated wires, coils, or thin films with positive TCR values. Because RTDs are most commonly made from pure metals with specific geometric constraints and conformational limitations, many challenges are faced when trying to miniaturize or to make flexible devices for use in smart textiles.

$$R = \frac{V}{I} \quad (2)$$

Detector testing and characterization included SEM imaging, TGA, and DC electrical measurements of the FRTD in a humidity and temperature-controlled box. SEM imaging utilized a JEOL JSM-7401F (Japan) field emission scanning electron microscope with an accelerating voltage of 1.5-kilovolts and a 13-millimeter working distance. TGA thermographs were acquired using a TA Instruments Q500 thermogravimetric analyzer with a platinum boat at a ramp rate of 10-° C./min up to 600-° C. DC measurements were obtained using a Solartron 1470E (UK) multichannel potentiostat/galvanostat, by applying a 1-volt potential and measuring current at either constant-humidity/variable-temperature, or constant-temperature/variable-humidity. The box conditions were controlled using a J-KEM Apollo temperature controller and Omega Engineering HX15 (USA) humidity probe with OM-CP-QUADPROCESS-25MA data logger. The humidity was controlled at 0% and 25% RH with dry and humid airflow at a rate of 400-ccm. The temperature ramp was 30° C./hour from 25° C. to 45° C. Testing equipment used to test the FRTD included 1) Omega Engineering HX15 humidity and temperature probe with OM-CPQUADPROCESS-25MA data logger to monitor and record the humidity during testing, 2) Humidity and Temperature Controlled box with two electrical terminals where the FRTD was tested, 3) J-KEM Apollo temperature controller to control the box temperature, 4) Dry and wet air flow meters to control humidity inside the box, 5) Solartron 1470E Multichannel potentiostat/galvanostat to apply the potential and record the current across the FRTD.

Sensor Evaluation

Figure 8:
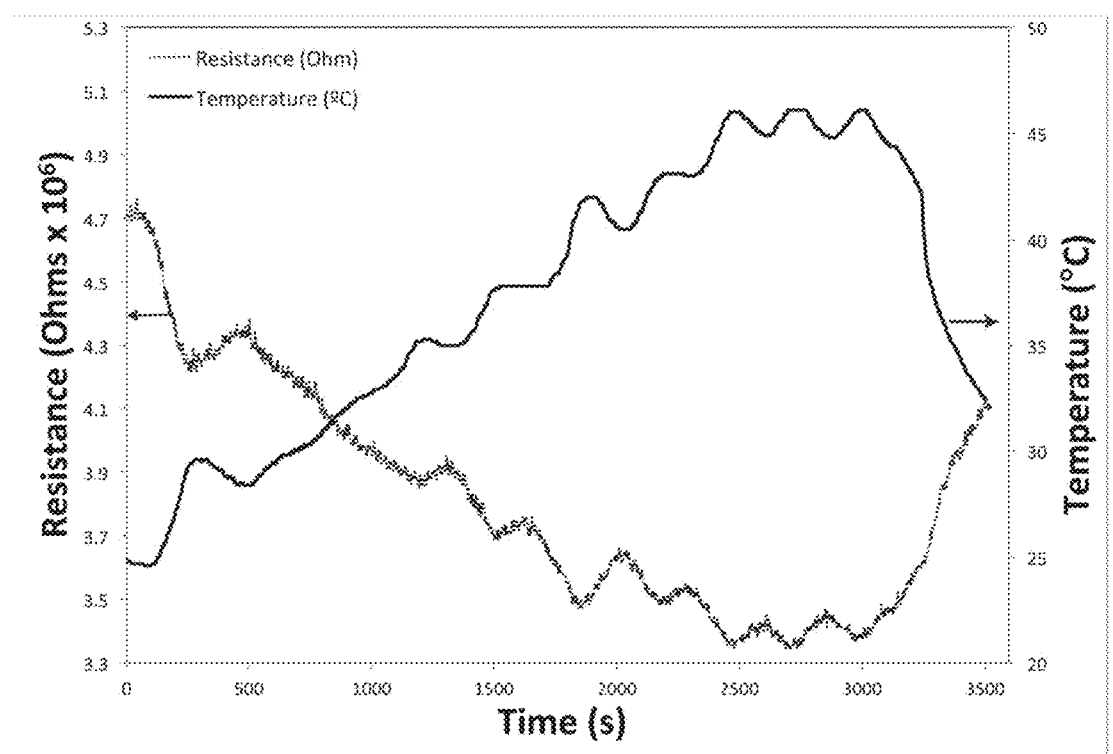
FIG. 8 is a graph showing the FRTD resistance changing with changing temperature from 25° C. to 45° C. at 30° C. per hour. This illustrates the fast temperature response and demonstrates the resistance returning to its initial value as the material cools back down towards 25° C.
Figure 9:
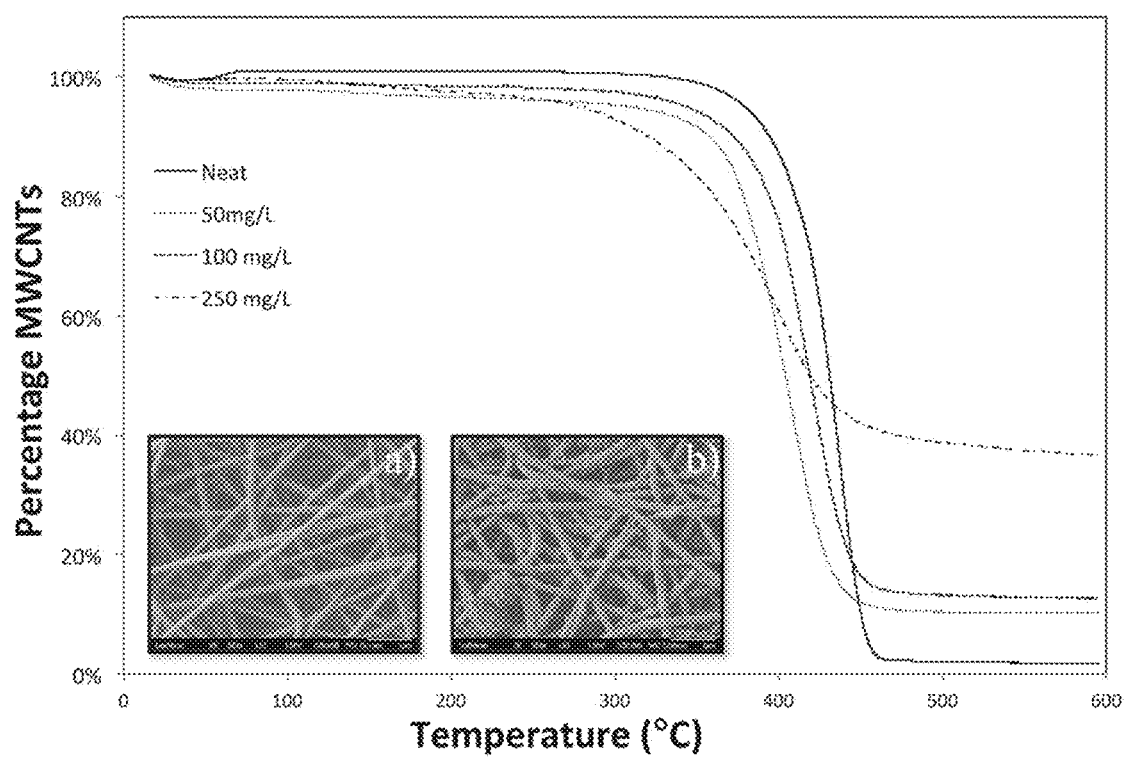
FIG. 9 is a TGA thermograph showing how changing the MWCNT solution concentration changes the weight percent of MWCNTs on the nylon-6 scaffold, as well as SEM images of a) neat nylon-6 nanofibers, and b) MWCNT functionalized nylon-6 nanofibers.

Nylon-6/MWCNT/PPy nanocomposite sensor successfully determined changes in temperature. FIG. 8 shows how the resistance of the FRTD changes when the temperature is ramped from 25° C. to 45° C. at a rate of 30° C. per hour. Notably, the detector resistance is sensitive towards temperature changes and responds quickly to minor fluctuations. These are directly indicated by the inverse fluctuations in the material's resistance as indicated in FIG. 8. This is optimal for detecting temperature changes in a short range with great accuracy. FIG. 9 shows a TGA thermograph of nylon-6 membranes functionalized using varying MWCNT concentrations in the filtration solution. The structure of the neat and MWCNT functionalized nanofibers are seen in the SEM images inset in FIG. 9. FIG. 9a shows the bare nylon-6 fibers before functionalization. The nylon-6 fibers range in diameter from 123 to 180-nanometers and the fiber mat porosity ranges from 0.86 to 0.89. FIG. 9b shows the nylon-6 fibers after functionalization with MWCNTs. Many of the nanotubes conglomerate into bundles and lay individually on the nanofibers, creating a disconnected network that leads to high resistances of the matrix before pyrrole polymerization.

Figure 10:
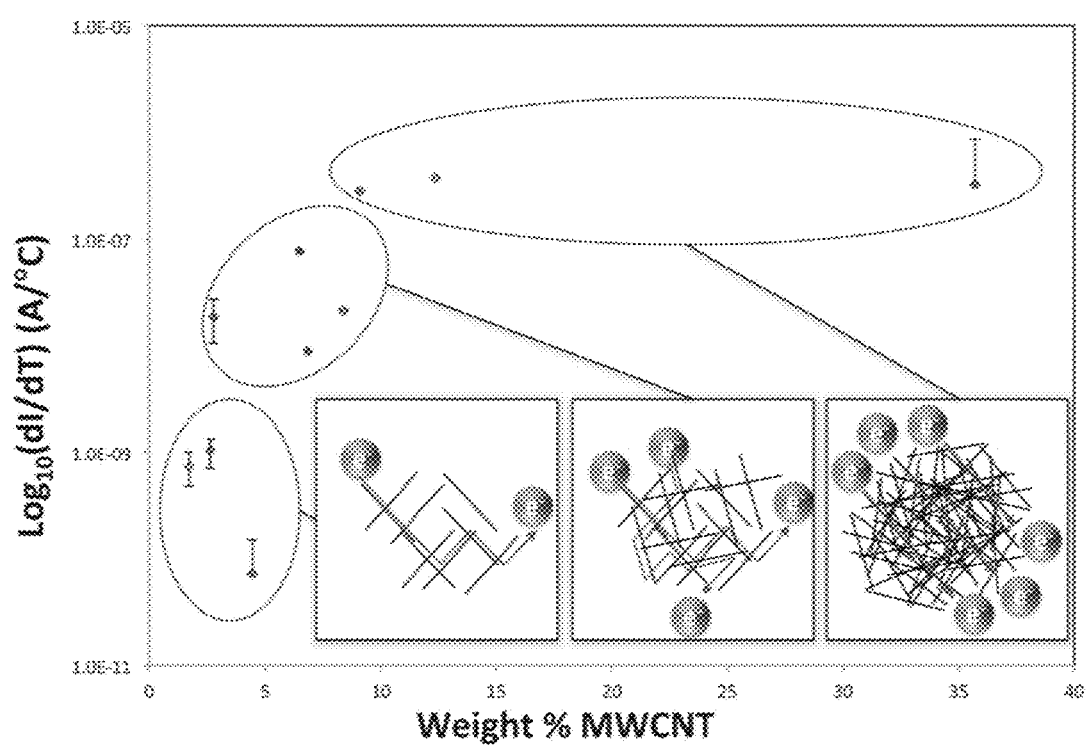
FIG. 10 represents the detector response as a function of the weight percent of MWCNTs loaded onto the nylon-6 substrate. The amount of MWCNTs on the nanocomposite surface dictates the overall amount of current that can be passed through the detector, limiting the sensitivity of the detector.

TGA analysis determined the MWCNT loading on the nylon-6 substrate. The concentration of MWCNTs in the filtration solution increases as the weight percent of nanotubes on the matrix also increases. FIG. 10 shows the effect that MWCNT loading has on detector response. Detector response is defined as the linear change in current with respect to the linear change in temperature. The material displays a percolative behavior dependent upon the MWCNT loading as described by the illustrations in FIG. 10. For smaller weight percent MWCNT loadings, fewer electrons are able to pass over the surface, but as the amount of nanotubes on the surface increases, so do the conductive pathways for electrons to flow across. This behavior happens as the weight percent nanotubes on the scaffold increases until approximately 10% to 11% MWCNTs, where there are so many conductive pathways, that the only resistance to electron flow is the inherent material properties of the materials of which they flow through. A low percolation threshold corresponds to below about 2% for MWCNT/nylon-6 nanocomposites.

Figure 11:
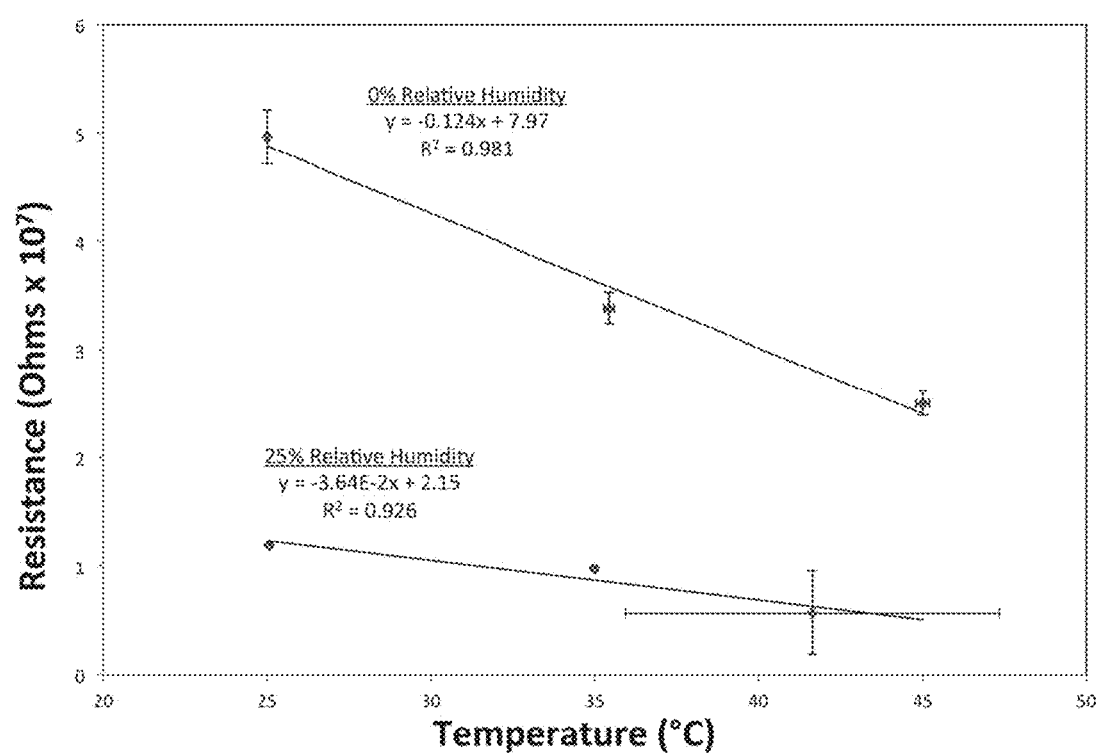
FIG. 11 is a graph showing the compounding effect of temperature and humidity on the material resistance.
Figure 12:
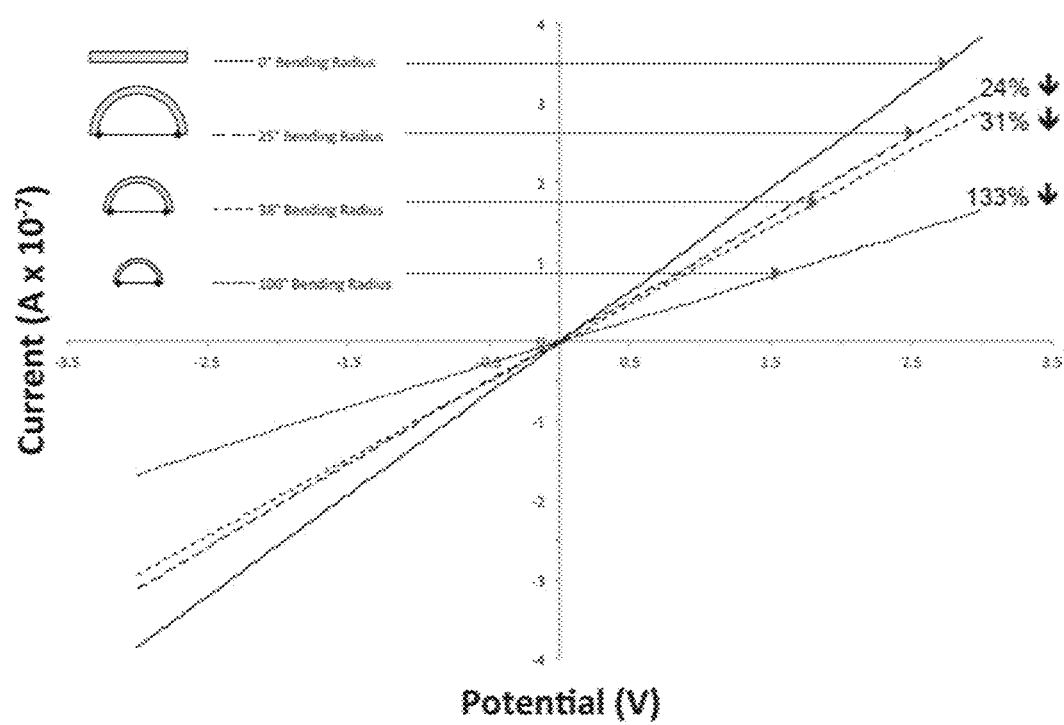
FIG. 12 is a graph showing how the characteristic current-voltage behavior of the FRTD changes with bending of the material.

FIG. 11 shows detector response as a function of temperature and humidity. The FRTD material with the highest conductivity and detector response was chosen for humidity and temperature testing. As temperature and humidity increase, the FRTD resistance decreases. As in typical RTDs, the detector response is linear in the desired temperature range. This is an advantage of using resistive devices as opposed to thermistors and thermocouples, which characteristically have nonlinear curves and require intensive calibrations. This change in resistance can be used to indicate the initialization of uncomfortable stump-socket conditions or over exhaustion for people doing hot work. For example, a decrease in detector resistance indicates that the environment being detected is warming, which would initiate a cooling mechanism at a predefined temperature and resistance. If cooling were insufficient, an increase in humidity due to the presence of sweat would alert the user of the potential for uncomfortable or damaging conditions. In FIG. 12 the effect of bending the FRTD material is described using the current-voltage characteristic of the material. It is seen that bending does have an effect on the material characteristic, which should be considered when applying this detector to a device. It is seen that a small bending radius of 25° produces a small, approximately 24% change in the characteristic electrical behavior of the material.

Nanocomposite characterization shows percolation behavior at the material surface and conductive interconnectivity can be used to understand the device's increase in conductivity with increasing MWCNT loading. The nanocomposite resistance decreases with both increasing temperature and humidity, allowing its use as an indicator for uncomfortable or dangerous conditions.

What is claimed is:

1. A flexible fabric electrode sensor adapted to contact an exterior epithelium surface comprising:
    a flexible fabric composite including a flexible non-conductive fabric substrate, a flexible conductive fabric intermediate layer, and a top calixarene layer formed on the intermediate layer; and
    a first electrode and a second electrode communicating with a controller to assess electric current across said flexible fabric composite, wherein sodium ions form a supramolecular complex with said top calixarene layer, wherein said supramolecular complex impedes charge carrier mobility and thus affects said electric current across said flexible fabric composite as assessed by said controller to provide in-situ detection of a physiological salt component in sweat or other aqueous body fluids at the exterior epithelium surface.

2. The flexible fabric electrode sensor of claim 1, wherein the flexible substrate is a polyamide.

3. The flexible fabric electrode sensor of claim 2, wherein the polyamide is nylon-6.

4. The flexible fabric electrode sensor of claim 1, wherein the flexible non-conductive fabric substrate is a scrim, sock, mat, scaffold, or textile.

5. The flexible fabric electrode sensor of claim 1, wherein the intermediate layer is carbon.

6. The flexible fabric electrode sensor of claim 1, wherein the intermediate layer is graphene.

7. The flexible fabric electrode sensor of claim 1, wherein the intermediate layer comprises nanoparticles, nanofibers, nanotubes, or combinations thereof.

8. The flexible fabric electrode sensor of claim 7, wherein the nanotubes are multi-walled carbon nanotubes (MWCNTs).

9. The flexible fabric electrode sensor of claim 1, wherein the intermediate layer is formed by dip-coating.

10. The flexible fabric electrode sensor of claim 1, wherein the top calixarene layer is calix[4]arene.

11. The flexible fabric electrode sensor of claim 1, wherein said first and second electrodes communicate with said controller, said controller interpreting output signals to detect changes in Na+ ion concentration.

12. A flexible fabric electrode sensor adapted to contact an exterior epithelium surface comprising:
    a flexible fabric composite including a flexible non-conductive fabric substrate and a flexible conductive fabric intermediate layer and a top flexible layer of polypyrrole (PPY) formed on the intermediate layer,
    a first electrode and a second electrode communicating with a controller to assess electric current across said flexible fabric composite, wherein charge carrier mobility increases as the temperature, humidity, or combinations thereof increases at the surface, and thus affects said electric current across said flexible fabric composite as assessed by said controller to provide in-situ detection of surface temperature, humidity, or combinations thereof at the exterior epithelium.

13. The flexible fabric electrode sensor of claim 12, wherein the intermediate layer comprises nanoparticles, nanofibers, nanotubes, or combinations thereof.

14. The flexible fabric electrode sensor of claim 13, wherein the nanotubes are multi-walled carbon nanotubes (MWCNTs).

15. The flexible fabric electrode sensor of claim 12, wherein said first and second electrodes communicate with said controller, said controller interpreting output signals to detect changes in temperature and humidity.

* * * * *